United States Patent [19]

Sassiver et al.

[11] 4,343,938
[45] Aug. 10, 1982

[54] 7-[Dα-(COUMARIN-3-CARBOX-AMIDO)ARYLACETAMIDO]-CEPHALOSPORANIC ACIDS OR SALTS

[75] Inventors: Martin L. Sassiver, Monsey, N.Y.; James H. Boothe, Montvale, N.J.

[73] Assignee: American Cyanamid Company, Stamford, Conn.

[21] Appl. No.: 304,757

[22] Filed: Sep. 23, 1981

Related U.S. Application Data

[62] Division of Ser. No. 889,675, Mar. 24, 1978, Pat. No. 4,317,774.

[51] Int. Cl.$^3$ .......................................... C07D 501/56
[52] U.S. Cl. ....................................... 544/27; 544/28
[58] Field of Search ................................... 544/27, 28

[56] References Cited

U.S. PATENT DOCUMENTS

4,064,241 12/1977 Ross et al. ............................ 544/27
4,172,198 10/1979 Kamiya et al. ...................... 544/27
4,285,941 8/1981 Machida et al. ..................... 544/27

*Primary Examiner*—Paul M. Coughlan, Jr.
*Attorney, Agent, or Firm*—Edward A. Conroy, Jr.

[57] ABSTRACT

This disclosure describes compounds of the class of 6-[D-α-(substituted-coumarin-3-carboxamido)-phenylacetamido]penicillanic acids which possess antimicrobial activity.

2 Claims, No Drawings

7-[Dα-(COUMARIN-3-CARBOX-AMIDO)ARYLACETAMIDO]-CEPHALOSPORANIC ACIDS OR SALTS

This is a division of application Ser. No. 889,675, filed Mar. 24, 1978, now U.S. Pat. No. 4,317,774.

BRIEF SUMMARY OF THE INVENTION

This invention relates to new derivatives of 6-aminopenicillanic acid and, more particularly, is concerned with novel compounds which may be represented by the following structural formula:

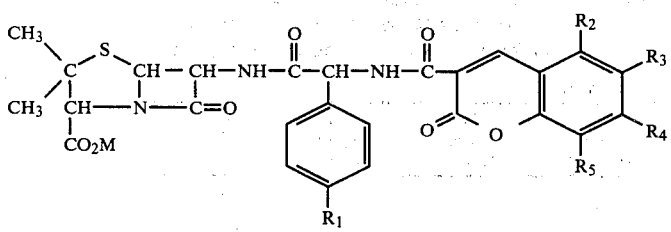

wherein $R_1$ is hydrogen or hydroxy; $R_2$ and $R_4$ are each individually selected from the group consisting of hydrogen, hydroxy, alkoxy having up to 4 carbon atoms, amino, monoalkylamino having up to 4 carbon atoms and dialkylamino having up to 4 carbon atoms in each alkyl group; $R_3$ and $R_5$ are each individually selected from the group consisting of hydrogen, hydroxy, alkyl having up to 4 carbon atoms, alkoxy having up to 4 carbon atoms, alkenyl having from 3 to 6 carbon atoms, alkanoyloxy having up to 4 carbon atoms, alkoxycarbonyloxy having up to 4 carbon atoms, chloro, bromo, nitro, amino, monoalkylamino having up to 4 carbon atoms, dialkylamino having up to 4 carbon atoms in each alkyl group, carboxy, phenyl, p-chlorophenyl and p-bromophenyl; $R_2$ and $R_3$ taken together, $R_3$ and $R_4$ taken together, and $R_4$ and $R_5$ taken together are each butadienylene; and M is hydrogen or a pharmaceutically acceptable non-toxic cation with the proviso that at least two of $R_2$, $R_3$, $R_4$ and $R_5$ must be hydrogen.

DETAILED DESCRIPTION OF THE INVENTION

Suitable alkyl and alkoxy groups contemplated by the present invention are, for example, methyl, ethyl, isopropyl, sec-butyl, methoxy, ethoxy, n-propoxy, isobutoxy, and the like. Appropriate alkenyl groups may be, for example, allyl, methallyl, isopropenyl, 1-butenyl, crotyl, 3-butenyl, etc. Suitable alkanoyloxy and alkoxycarbonyloxy groups are, for example, acetyloxy, propionyloxy, isobutyryloxy, methoxycarbonyloxy, isopropoxycarbonyloxy, isobutoxycarbonyloxy, and the like. The pharmacologically acceptable cations embraced by M in the above general formula include, for example, the non-toxic metal cations such as the sodium ion, potassium ion, calcium ion, magnesium ion, as well as the organic amine cations such as the tri(lower alkyl)amine cations (e.g., triethylamine), procaine, and the like.

The novel compounds of the present invention may be readily prepared by condensing an ampicillin derivative of the formula:

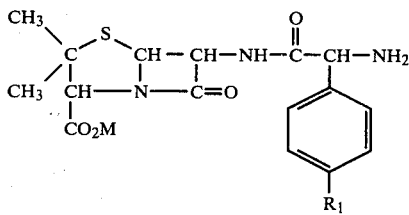

wherein $R_1$ and M are as hereinabove defined with a coumarin-3-carboxylic acid derivative of the formula:

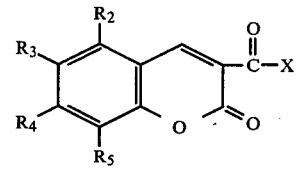

wherein $R_2$, $R_3$, $R_4$ and $R_5$ are as hereinabove defined and X is chloro or bromo as in an acid halide, or the moiety $-O-CO-OC_2H_5$ as in a mixed anhydride from ethyl chloroformate, or the moiety $-O-C(=N-cyclohexyl)NH-cyclohexyl$ as in a dicyclohexylcarbodiimide mediated reaction, or an azide function, or an azolide formed from carbonyldiimidazole. This acylation of the ampicillin derivative is best performed in an inert solvent such as tetrahydrofuran, dioxane, methylene chloride or chloroform (or mixtures thereof) at from ice bath temperature (about 0° C.) to room temperature (about 25° C.). The reaction is preferably carried out in the presence of an acid acceptor such as N-methylmorpholine, triethylamine, or soda ash and over a period of a few hours or more. The acylating agents may be prepared by methods well known in the art from the corresponding acids (X is hydroxy). Thus, an acid may be treated with a thionyl halide or oxalyl halide, if desired, in the presence of dimethylformamide, to yield the corresponding acyl halides (X is chloro or bromo), which can be converted to the acyl azides (X is $N_3$) by treatment with sodium azide.

The novel compounds of this invention may be physically characterized and their purity determined by any or all of the following methods: thin layer chromatography (t.l.c.), infrared spectroscopy (i.r.), nuclear magnetic resonance spectroscopy (n.m.r.), and high pressure liquid chromatography (h.p.l.c.). In t.l.c. an 80% n-propanol:20% water system with silica gel GF plates is used. Compounds appearing approximately at Rf 0.6 are detected by ultraviolet quenching and a toluidine-potassium iodide spray after chlorine fogging. In addition, these compounds are ninhydrin negative, whereas ampicillin [generally at a lower Rf (0.5)] is ninhydrin positive. In the i.r. spectra (potassium bromide disc), these compounds are characterized by peaks at 5.6–5.65μ (β-lactam) 5.8, 6 and 6.6μ (lactone and amide carbonyls). In the n.m.r. spectra (D-6-dimethylsulfoxide, 100 MHz), characteristic peaks appear at 9.7δ (d, 1H, amide), 9.3δ (d, 1H, amide), 9.4δ to 8.8δ (S, 1H, 4-H of coumarin ring), 8.6δ to 7.2δ (M-aromatic protons of coumarin and phenyl rings), 5.9δ (d, 1H, CH of phenylacetyl side chain), 5.55δ (q, 1H, H-6 of penam ring), 5.4δ (d, 1H, H-5 of penam ring), 1.55δ (S, 3H, CH₃ of penam), 1.4δ (S, 3H, other CH₃ of penam), with additional peaks characteristic of each compound. The h.p.l.c. is performed using a Partisil ODS (Water's Assoc.) column with a phosphate buffer (pH 7):acetonitrile (85:15)system on a Waters' high pressure instrument. By one or more of these methods, product purity of the compounds of this invention was established at 80–90%.

The novel compounds of the present invention are biologically active and have been found to possess antibacterial activity. As indicated, they are useful antimicrobial agents and have broad-spectrum antimicrobial activity in vitro against standard laboratory microorganisms used to screen for activity against pathogens. The antibacterial spectrum of typical compounds of the present invention, representing the concentration required to inhibit the growth of various typical bacteria, was determined in a standard manner by the agar-dilution streak-plate technique. A Steers multiple inocula replicator was employed with incubation at 37° C. for 18 hours in conventional nutrient agar. The results are set forth in Table I below expressed as the minimal inhibitory concentration in micrograms per milliliter.

TABLE I

| Compound | Pseudomonas aeruginosa UCS 7613 | Klebsiella pneumoniae MA 75-2 | Enterobacter cloacae OSU 75-2 | Proteus mirabilis OSU 75-3 | Proteus morganii K 72 | Escherichia coli CU 75-1 | Staphylococcus aureus OSU 75-2 |
|---|---|---|---|---|---|---|---|
| 6-[D-α-(6-Hydroxycoumarin-3-carboxamido)-phenylacetamido]penicillanic acid | 2 | 16 | 16 | 4 | 32 | 8 | 0.25 |
| 6-[D-α-(7-Methoxycoumarin)-3-carboxamido)-phenylacetamido]penicillanic acid | 1 | 8 | 16 | 2 | 16 | 8 | 1 |
| 6-[D-α-(8-Nitrocoumarin-3-carboxamido)phenylacetamido]penicillanic acid | 8 | 32 | 32 | 1 | 16 | 16 | 1 |
| 6-[D-α-(5-Azacoumarin-3-carboxamido)phenylacetamido]penicillanic acid | 4 | 128 | — | 1 | 128 | 16 | 0.5 |
| 6-[D-α-(5,7-Dimethoxycoumarin-3-carboxamido)-phenylacetamido]penicillanic acid | 2 | 128 | 32 | 16 | 64 | 16 | 1 |
| 6-[D-α-(5,6-Benzocoumarin-3-carboxamido)phenylacetamido]pencillanic acid | 2 | 16 | 16 | 2 | 32 | 4 | 0.12 |
| 6-[D-α-(8-Allylcoumarin-3-carboxamido)-phenylacetamido]penicillanic acid | 2 | 8 | 8 | 2 | 16 | 4 | 0.12 |
| 6-[D-α-(Coumarin-3-carboxamido)phenylacetamido]penicillanic acid | 2 | 16 | 16 | 4 | 16 | 8 | 2 |
| 6-[D-α-(5,6-Benzocoumarin-3-carboxamido)-p-hydroxyphenylacetamido]penicillanic acid | 2 | 64 | 64 | 4 | 64 | 16 | 0.5 |
| 6-[D-α-(6-Ethoxycarbonyloxycoumarin-3-carboxamido)phenylacetamido]-penicillanic acid | 2 | 16 | 32 | 4 | 32 | 8 | 0.25 |
| 6-[D-α-(6,8-Dichlorocoumarin-3-carboxamido)-phenylacetamido]penicillanic acid | 2 | 8 | 8 | 1 | 8 | 4 | 0.12 |
| 6-[D-α-(6,8-Dibromocoumarin-3-carboxamido)-phenylacetamido]penicillanic acid | 4 | 8 | 16 | 2 | 8 | 4 | 0.25 |
| 6-[D-α-(6-Phenylcoumarin-3-carboxamido)phenylacetamido]penicillanic acid | 2 | 4 | 8 | 2 | 8 | 2 | 0.12 |
| 6-[D-α-(6-Chlorocoumarin-3-carboxamido)phenylacetamido]penicillanic acid | 2 | 16 | 16 | 2 | 32 | 8 | 0.25 |
| 6-[D-α-(6-Carboxycoumarin-3-carboxamido)phenylacetamido]penicillanic | 128 | >128 | >128 | 64 | >128 | 64 | 4 |

TABLE I-continued

| Compound | Pseudomonas aeruginosa UCS 7613 | Klebsiella pneumoniae MA 75-2 | Enterobacter cloacae OSU 75-2 | Proteus mirabilis OSU 75-3 | Proteus morganii K 72 | Escherechia coli CU 75-1 | Staphylococcus aureus OSU 75-2 |
|---|---|---|---|---|---|---|---|
| 6-[D-α-(6,7-Benzocoumarin-3-carboxamido)-phenylacetamido]penicillanic acid | 1 | 8 | 4 | 0.5 | 16 | 16 | ≦0.06 |
| 6-[D-α-(6-p-chlorophenylcoumarin-3-carboxamido)phenylacetamido]-penicillanic acid | 16 | 16 | 32 | 8 | 16 | 16 | 1 |
| 6-[Dα-(6-Nitrocoumarin-3-carboxamido)phenylacetamido]penicillanic acid | 16 | 64 | 128 | 4 | 64 | 32 | 1 |
| 6-[D-α-(8-Aminocoumarin-3-carboxamido)phenylacetamido]penicillanic acid | 32 | >128 | >128 | 4 | 128 | 64 | 2 |
| 7-[D-α-(Coumarin-3-carboxamido)phenylacetamido]cephalosporanic acid | 8 | 32 | 32 | 16 | 128 | 32 | 0.5 |
| 6-[D-α-(7,8-Benzocoumarin-3-carboxamido)-phenylacetamido]penicillanic acid | 4 | 16 | 16 | 1 | 16 | 8 | 0.5 |
| Carbenicillin | 32 | >128 | 32 | 1 | 128 | 8 | 0.5 |
| Ampicillin | >128 | 16 | >128 | 0.25 | >128 | 1 | 0.12 |
| 6-[D-α-(7,8-Benzocoumarin-3-carboxamido)-phenylacetamido]penicillanic acid | 2 | 16 | 8 | 4 | 16 | 8 | 0.12 |
| 6-[D-α-(7-Diethylaminocoumarin-3-carboxamido)phenylacetamido]penicillanic acid | 1 | 4 | 4 | 4 | 8 | 8 | 0.25 |
| 7-[D-α-(Coumarin-3-carboxamido)phenylacetamido]-3-[(1-methyltetrazole-5-thio)methyl]ceph-3-em-4-carboxylic acid | 4 | 16 | 16 | 4 | 32 | 32 | 0.5 |

A preferred embodiment of the present invention may be represented by the following structural formula:

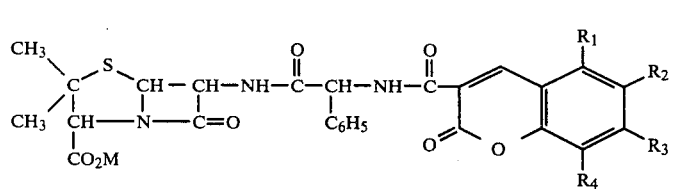

wherein $R_1$ and $R_3$ are each individually selected from the group consisting of hydrogen, hydroxy, methoxy and ethoxy; $R_2$ and $R_4$ are each individually selected from the group consisting of hydrogen, hydroxy, methyl, ethyl, methoxy, ethoxy, allyl, methallyl, nitro, amino, chloro, bromo and phenyl; $R_1$ and $R_2$ taken together, $R_2$ and $R_3$ taken together, and $R_3$ and $R_4$ taken together are each butadienylene; and M is hydrogen or a pharmacologically acceptable cation with the proviso that at least two of $R_1$, $R_2$, $R_3$ and $R_4$ must be hydrogen.

A most preferred embodiment of the present invention may be represented by the following structural formula:

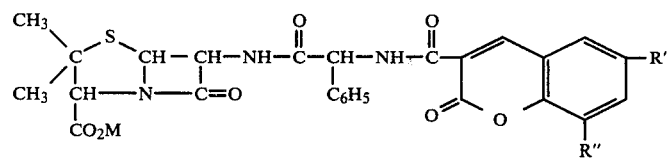

wherein R' and R'' are each individually selected from the group consisting of hydrogen, hydroxy, methoxy, ethoxy, chloro and bromo and M is hydrogen or a pharmaceutically acceptable cation.

The invention will be described in conjunction with the following specific examples.

EXAMPLE 1

6-[D-α-(5,6-Benzocoumarin-3-carboxamido)-phenylacetamido]penicillanic acid

To a suspension of 483 mg. of 5,6-benzocoumarin-3-carboxylic acid in 45 ml. of dioxane and 10 ml. of acetone is added 0.282 ml. of triethylamine. The mixture is cooled and stirred in an ice bath and 0.194 ml. of ethyl chloroformate is added dropwise over 10 minutes. Stirring and cooling is continued another 45 minutes. Then 0.281 ml. of triethyl amine and 807 mg. of ampicillin trihydrate are added. Stirring and cooling is continued another hour. A chilled mixture of 3 ml. of saturated sodium bicarbonate solution and 35 ml. of water is added and the reaction mixture is shaken with 100 ml. of ethyl acetate. The mixture is filtered to remove suspended solids. The aqueous layer is acidified, with cooling, with 6 N hydrochloric acid to pH 2 and then extracted with 100 ml., then 50 ml. of ethyl acetate. The combined ethyl acetate extracts are washed with 25 ml. of water, dried over magnesium sulfate and evaporated to a solid. Trituration with ether and filtration gives the desired product, i.r. 5.4μ (β lactam).

EXAMPLE 2

6-[D-α-(8-Allylcoumarin-3-carboxamido)-phenylacetamido]penicillanic acid

To a stirred solution of 430 mg. of 8-allylcoumarin-3-carboxylic acid [R. R. Bui-Hoi, et al., *Bull. Soc. Chim. Fr.*, 128 (1947)] and 0.225 ml. of N-methylmorpholine in 25 ml. of methylene chloride and 25 ml. of dioxane, cooled in an ice-methanol bath to −10° to −12° C., is added 0.192 ml. of ethyl chloroformate dropwise. After 8 minutes, 0.223 ml. of N-methylmorpholine and 807 mg. of ampicillin trihydrate are added. The ice-methanol bath is replaced with an ice bath, and after one additional hour a chilled mixture of 20 ml. of dioxane, 10 ml. of acetone, 35 ml. of water and 3 ml. of saturated sodium bicarbonate is added. The reaction mixture is worked up as described in Example 1 (except no filtration of the two phase mixture is necessary). Trituration of the product with ether-hexane and filtration gives the desired product, i.r. 5.62μ (β lactam).

EXAMPLE 3

6-[D-α-(Coumarin-3-carboxamido)]phenylacetamido]-penicillanic acid

This product is prepared as described in Example 2, except that the starting material is 382 mg. of coumarin-3-carboxylic acid. The desired product is obtained, i.r. 5.67μ (β lactam).

EXAMPLE 4

6-[D-α-(5,6-Benzocoumarin-3-carboxamido)-p-hydroxyphenylacetamido]penicillanic acid To a suspension of 483 mg. of 5,6-benzocoumarin-3-carboxylic acid and 0.225 ml. of N-methylmorpholine in 25 ml. of dioxane and 25 ml. of methylene chloride, cooled to −10° to −15° C. in an ice-methanol bath, is added 0.192 ml. of ethyl chloroformate dropwise over several minutes. After an additional 25 minutes of stirring and cooling, 0.223 ml. of N-methylmorpholine and 770 mg. of amoxicillin are added. The mixture is stirred in an ordinary ice bath for one hour. Then a cold mixture of 20 ml. of dioxane, 10 ml. of acetone, 35 ml. of water and 3 ml. of saturated sodium bicarbonate is added. Workup is done as described in Example 1 giving the desired product, i.4. 5.65μ (β lactam).

EXAMPLE 5

6-[D-α-(6-Ethoxycarbonyloxycoumarin-3-carboxamido)phenylacetamido]penicillanic acid This product is prepared as described in Example 2, except that 417 mg. of 6-hydroxycoumarin-3-carboxylic acid [F. D. Cramer & H. Windel, *Chem. Ber.*, 89, 354 (1956)], 0.564 ml. of triethylamine, 0.388 ml. of ethyl chloroformate, ice bath (0°–5° C.) temperature and a one hour reaction time are used to form the mixed anhydride. Reaction with ampicillin and workup gives the desired product, i.r. 5.67μ (β lactam).

EXAMPLE 6

6-[D-α-(6-Hydroxycoumarin-3-carboxamido)-phenylacetamido]penicillanic acid

This product is prepared as described in Example 5, except that 0.225 ml. of N-methylmorpholine, 0.192 ml. of ethyl chloroformate, and a reaction time of 15 minutes at −10° C. plus 30 minutes at 0° C. are used to form the mixed anhydride. Reaction with ampicillin (using 0.223 ml. of N-methylmorpholine) and workup as in Example 5 gives 343 mg. of crude product. Removal of some starting 6-hydroxycoumarin-3-carboxylic acid from the product is accomplished by stirring 243 mg. of crude product with ethyl acetate, filtering and evaporating the ethyl acetate to dryness giving the purified product, i.r. 5.66μ (β lactam).

EXAMPLE 7

6-[D-α-(7-methoxycoumarin-3-carboxamido)-phenylacetamido]penicillanic acid

To a solution of 444 mg. of 7-methoxycoumarin-3-carboxylic acid [W. Baker & C. B. Collis, *J. Chem. Soc.*, 5, 12–15 (1949)] and 0.282 ml. of triethylamine in 25 ml. of dioxane and 25 ml. of methylene chloride, stirred and cooled in an ice bath, is added 0.194 ml. of ethyl chloroformate dropwise. After 25 minutes, 0.281 ml. of triethylamine and 807 mg. of ampicillin trihydrate are added. After an additional one hour of reaction at 0°–5° C., workup as described in Example 4 gives the desired product, i.r. 5.61μ (β-lactam).

EXAMPLE 8

6-[D-α-(8-Nitrocoumarin-3-carboxamido)-phenylacetamido]-penicillanic acid

This reaction is performed as described in Example 7, using 475 mg. of 8-nitrocoumarin-3-carboxylic acid [R. O. Clinton and S. G. Laskowski, *J. Am. Chem. Soc.*, 71, 3662 (1949)]. The desired product is obtained, i.r. 5.60μ (β-lactam).

EXAMPLE 9

6-[D-α-(5-Azacoumarin-3-carboxamido)-phenylacetamido]penicillanic acid

This reaction is performed as described in Example 7, using 386 mg. of 5-azacoumarin-3-carboxylic acid [R. B. Moffitt, *J. Org. Chem.*, 35, 3596 (1970)]. The desired product is obtained, i.r. 5.63μ (β-lactam).

EXAMPLE 10

6-[D-α-(5,7-Dimethoxycoumarin-3-carboxamido)-phenylacetamido]penicillanic acid

A 0.5 g. portion of 5,7-dimethoxycoumarin-3-carboxylic acid [A. Roberston and T. S. Subramaniam, *J. Chem. Soc.*, 286 (1937)] is reacted with 0.195 ml. of ethyl chloroformate and 0.28 ml. of triethylamine. Then 0.28 ml. of triethylamine and 0.8 g. of ampicillin trihydrate are added according to the procedure of Example 1 giving the desired product, i.4. 5.61μ (β lactam).

EXAMPLE 11

6-[D-α-(6,8-Dichlorocoumarin-3-carboxamido)-phenylacetamido]penicillanic acid

A 0.518 g. portion of 6,8-dichlorocoumarin-3-carboxylic acid [Ng. Ph. Bui-Hoi, et al., *Bull Soc. Chim. Fr.*, 561 (1957)] is reacted with 0.195 ml. of ethyl chloroformate and 0.28 ml. of triethylamine. Then 0.28 ml. of triethylamine and 0.8 g. of ampicillin trihydrate are added according to the procedure of Example 1, giving the desired product, i.r. 5.65μ (β lactam).

EXAMPLE 12

6-[D-α-(6,8-Dibromocoumarin-3-carboxamido)-phenylacetamido]penicillanic acid

A 0.692 g. portion of 6,8-dibromocoumarin-3-carboxylic acid [Ng. Ph. Bui-Hoi, et al., *Bull. Soc. Chim. Fr.*, 561 (1957)] is reacted with 0.195 ml of ethylchloroformate and 0.28 ml. of triethylamine. Then 0.28 ml. of triethylamine and 0.8 g. of ampicillin trihydrate are added according to the procedure of Example 1, giving the desired product, i.r. 5.63μ (β lactam).

EXAMPLE 13

6-[D-α-(6-Phenylcoumarin-3-carboxamido)-phenylacetamido]penicillanic acid

A 0.27 g. portion of 6-phenylcoumarin-3-carboxylic acid is reacted with 0.095 ml. of ethyl chloroformate and 0.14 ml. of triethylamine. Then 0.14 ml. of triethylamine and 0.4 g. of ampicillin trihydrate are added according to the procedure of Example 1, giving the desired product, i.r. 5.67μ (β lactam).

EXAMPLE 14

6-[D-α-(6-Chlorocoumarin-3-carboxamido)-phenylacetamido]penicillanic acid

A 0.45 g. portion of 6-chlorocoumarin-3-carboxylic acid [L. L. Woods and J. Sapp, *J. Org. Chem.*, 30, 312 (1965)] is reacted with 0.195 ml. of ethyl chloroformate and 0.28 ml. of triethylamine. Then 0.28 ml. of triethylamine and 0.8 g. of ampicillin trihydrate are added according to the procedure of Example 1, giving the desired product, i.r. 5.68μ (β lactam).

EXAMPLE 15

6-[D-α-(6-Carboxycoumarin-3-carboxamido)-phenylacetamido]penicillanic acid

To a suspension of 400 mg. of 6-carboxycoumarin-3-carboxylic acid [R. Selleri, *Arzn. Forsch.*, 15, 910 (1965)] and 0.38 ml. of N-methylmorpholine in 25 ml. of dioxane and 25 ml. of methylenechloride, cooled to −15° C. in an ice-methanol bath, is added 0.323 ml. of ethyl chloroformate dropwise. Then more solvent is added and the reaction held at 0° C. for 30 minutes. Addition of 0.19 ml. of N-methylmorpholine and 685 mg. of ampicillin trihydrate gives, after the two isomeric compounds derived from reaction of either the 6- or 3-carboxy group of the starting acid. Separation by chromatography gives the desired product, i.r. 5.62μ (β lactam).

EXAMPLE 16

6-[D-α-(6,7-Benzocoumarin-3-carboxamido)-phenylacetamido]penicillanic acid

This compound is prepared similarly to the 5.6-benzo analog of Example 1. Thus, 336 mg. of carboxylic acid [T. Boehm and E. Profft, *Arch. Pharm.*, 269, 25 (1931)] gives the desired compound, i.r. 5.67μ (β lactam).

EXAMPLE 17

6-[D-α-(6-p-Chlorophenylcoumarin-3-carboxamido)-phenylacetamido]penicillanic acid This compound is prepared similarly to Example 1. Thus, 202 mg. of carboxylic acid gives the desired compound, i.r. 5.63μ (β lactam).

EXAMPLE 18

6-(p-Chlorophenyl)coumarin-3-carboxylic acid 4-(p-Chlorophenyl)phenol is converted via the Duff reaction [*J. Chem. Soc.*, 547 (1941)] to 2-hydroxy-5-(p-chlorophenyl)benzaldehyde, mp. 74°–78° C. i.r. 6.02μ. A solution of 2]3 mg. (1 mmole) of this aldehyde, 0.4 ml. (2.63 mmole) of diethylmalonate and 0.2 ml. (2 mmole) of piperidine is heated for 10 minutes and kept at 25° C. for 2 hours. Then 5 ml. of 9 N HCl is added and the mixture stirred at reflux overnight. The mixture is cooled in an ice bath and filtered to yield 238 mg. of the desired compound, i.r. 5.74, 5.9μ.

EXAMPLE 19

6-[D-α-(6-Nitrocoumarin-3-carboxamido)-phenylacetamido]penicillanic acid

This compound is prepared similarly to the 8-nitro analog of Example 8 to give the desired product, i.r. 5.60μ (β lactam). The 6-nitrocoumarin-3-carboxylic acid is obtained after Lampe and Macierwicz, *Roezniki Chem.*, 18, 668 (1938).

EXAMPLE 20

6-[D-α-(8-Aminocoumarin-3-carboxamido)-phenylacetamido]penicillanic acid

This compound is prepared by reduction of 125 mg. of the 8-nitro analog of Example 8 with hydrogen and 25 mg. of 10% Pd/C in ethanol to give the desired product, i.r. 5.65μ (β lactam).

EXAMPLE 21

7-[D-α-(Coumarin-3-carboxamido)phenylacetamido]-cephalosporanic acid

To a solution of 190 mg. of coumarin-3-carboxylic acid and 0.141 ml. of triethylamine in 12 ml. of dioxane and 12 ml. of methylene chloride is added 0.097 ml. of ethyl chloroformate at 0°–5° C. After 30 minutes, 0.141 ml. of triethylamine and one mmole of cephaloglycin are added. After one hour at 5° C., typical workup gives the desired product, i.r. 5.64μ (β lactam).

EXAMPLE 22

6-[D-α-(7,8-Benzocoumarin-3-carboxamido)-phenylacetamido]penicillanic acid

This compound is prepared as described in Example 1, i.r. 5.65μ (β lactam). The acid is prepared after F. D. Cramer and H. Windel, *Chem. Ber.*, 89, 354 (1956).

EXAMPLE 23

6-[D-α-(6-Methylcoumarin-3-carboxamido)-phenylacetamido]penicillanic acid

From 412 mg. of 6-methylcoumarin-3-carboxylic acid [B. Reichert and W. Hoss, *Arch. Pharm.*, 280, 157 (1942)], 0.282 ml. of triethylamine and 0.194 ml. of ethylchloroformate is prepared the mixed anhydride. Reaction with 0.281 ml. of triethylamine and 807 mg. of ampicillin.3H$_2$O gives 567 mg. of product.

EXAMPLE 24

6-[D-α-(7-Diethylaminocoumarin-3-carboxamido)-phenylacetamido]penicillanic acid

To a solution of 527 mg. (2.02 mmoles) of 7-diethylaminocoumarin-3-carboxylic acid [mp. 227°–229° C., from hydrolysis of ethyl 7-diethylaminocoumarin-3-carboxylate (J. D. Kendall, et al., Ilford Ltd., Brit. Pat. 867,592; *Chem. Abstr.*, 55, 21927-C)], 0.282 ml. (2.04 mmoles) of triethylamine in 25 ml. of methylene chloride and 25 ml. of dioxane is added 0.194 ml. (2.04 mmole) of ethylchloroformate, dropwise, at 0°–5° C. over 10 minutes. After 30 minutes, 0.281 ml. of triethylamine and 807 mg. of ampicillin trihydrate are added and the mixture stirred for one hour. The aqueous phase from an aqueous bicarbonate-ethyl acetate quench of the reaction mixture is acidified to pH 2.5. Extraction with ethyl acetate and evaporation gives 773 mg. of the desired product.

EXAMPLE 25

7-[D-α-(Coumarin-3-carboxamido)phenylacetamido]-3-[(1-methyltetrazole-5-thio)methyl]ceph-3-em-4-carboxylic acid A mixture of 288 mg. (0.5 mmole) of the compound described in Example 21, 84 mg. (1 mmole) of sodium bicarbonate and 87 mg. (0.75 mmole) of 1-methyltetrazole-5-thiol in 8 ml. of 0.1 M pH 6.4 phosphate buffer and 10 ml. of acetone is heated under reflux at 50°–55° C. (oil bath) for 3 hours. Then an additional 58 mg. of the tetrazole and 60 mg of sodium bicarbonate (in 5 drops of water) are added and the solution heated overnight. The acetone is removed in vacuo and the cooled aqueous residue acidified to pH 2.2 to precipitate a white solid. This is filtered off, washed with water and dried to give 262 mg., i.r. (KBr) 5.60μ (β lactam).

We claim:

1. A compound selected from the group consisting of 7-[D-α-(coumarin-3-carboxamido)phenylacetamido]-cephalosporanic acid and the pharmacologically acceptable cationic salts thereof.

2. A compound selected from the group consisting of 7-[D-α-(coumarin-3-carboxamido)phenylacetamido]-3-[(1-methyltetrazole-5-thio)methyl]ceph-3-em-4-carboxylic acid and the pharmacologically acceptable cationic salts thereof.

* * * * *